(12) United States Patent
Floyd et al.

(10) Patent No.: US 6,346,529 B1
(45) Date of Patent: Feb. 12, 2002

(54) ANTIVIRAL THERAPY USING THIAZINE DYES

(75) Inventors: Robert A. Floyd, Oklahoma City, OK (US); Raymond F. Schinazi, Decatur, GA (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/060,670

(22) Filed: Apr. 15, 1998

Related U.S. Application Data

(60) Division of application No. 08/707,992, filed on Jul. 12, 1996, now Pat. No. 5,827,644, which is a continuation of application No. 08/251,624, filed on May 31, 1994, now Pat. No. 5,571,666, which is a continuation of application No. 08/029,984, filed on Mar. 12, 1993, now abandoned, which is a continuation of application No. 07/758,228, filed on Sep. 9, 1991, now abandoned, which is a continuation of application No. 07/632,606, filed on Dec. 24, 1990, now abandoned, which is a continuation of application No. 07/350,383, filed on May 11, 1989, now abandoned, which is a continuation-in-part of application No. 07/264,088, filed on Oct. 28, 1988, now Pat. No. 4,950,665.

(51) Int. Cl.[7] .............................................. A61K 31/54
(52) U.S. Cl. ................... 514/226.2; 514/224.2; 514/224.8
(58) Field of Search ............................ 514/226.2, 224.2, 514/224.8

(56) References Cited

U.S. PATENT DOCUMENTS

| | | |
|---|---|---|
| 3,557,783 A | 1/1971 | Castner |
| 3,829,578 A | 8/1974 | Fleming et al. |
| 4,139,348 A | 2/1979 | Swartz |
| 4,169,841 A | 10/1979 | Kelly |
| 4,181,128 A | 1/1980 | Swartz |
| 4,243,751 A | 1/1981 | Swartz |
| 4,305,390 A | 12/1981 | Swartz |
| 4,346,172 A | 8/1982 | Swartz |
| 4,402,318 A | 9/1983 | Swartz |
| 4,407,282 A | 10/1983 | Swartz |
| 4,775,625 A | 10/1988 | Sieber |
| 4,950,665 A | 8/1990 | Floyd |
| 5,091,385 A * | 2/1992 | Gulliya et al. ............ 514/224.8 |
| 5,120,649 A | 6/1992 | Horowitz et al. |
| 5,386,837 A | 2/1995 | Sterzer |
| 5,571,666 A | 11/1996 | Floyd et al. |

FOREIGN PATENT DOCUMENTS

EP      0 510 668 A2    4/1992

OTHER PUBLICATIONS

Ahfa "Unclassified Therapeutic Agents 92:00: Methylene Blue," pp. 2175–2177.

Floyd, et al. "Mediation of 8–Hydroxy–Guanine Formation in DNA by Thiazine Dyes Plus Light" *Free Rad. Biol. & Med.* 8: 327–330, (1990).

Floyd, et al. "Methylene Blue plus Light Mediates 8 Hydroxyguanine Formation in DNA", *Arch. Biochem. Biophys* 273: 106–111 (1989).

(List continued on next page.)

*Primary Examiner*—Russell Travers
(74) *Attorney, Agent, or Firm*—Holland & Knight LLP

(57) ABSTRACT

A method for using thiazine dyes, especially methylene blue, alone or in combination with low levels of light, to selectively inactivate or inhibit intracellular replication of specific viruses, especially human immunodeficiency virus. Examples of useful thiazine dyes are methylene blue, azure A, azure C, toluidine blue O, and thionine. The preferred dye at this time is methylene blue. Methylene blue is FDA approved for topical, i.v., and oral administration, and has minimal side effects. Since methylene blue absorbs in the red wavelengths, i.e., approximately 670 nm, which penetrates tissue much better than other lower wavelengths, light penetrating the skin to the capillaries at the surface can be used to enhance the activity of the dye.

10 Claims, 1 Drawing Sheet

OTHER PUBLICATIONS

Lambrecht, et al. "Rapid Inactivation of HIV–1 in Single Donor Preparations of Human Fresh Frozen Plasma by Methylene Blue Light Treatment" *Biologicals* 22(3): 227–231 (1994).

Lenard, et al. "Photodynamic inactivation of inefectivity of human immunodeficiency virus and other enveloped viruses using hypercin and rose bengal: Inhibition of fusion and syncytia formation," *Proc. Natl. Acad. Sci.* 90: 158–162 (1993).

Martin, et al. "Oxygen Radicals are Generated by Dye–Mediated Intracellular Photoxidations: A Role for Superoxide in Photodynamic Effects" Matthews, et al., "Photodynamic therapy of viral contaminants with potential for blood banking applications," *Transfusion* 28:81–83 (1988).

McBride, et al. "Mutations induced by Methylene blue plus light in single stranded M13mp2" *Proc. Natl. Acad. Sci. USA* 89: 6866–6870 (1992).

Mohr, "Durch Methylenblau/Licht– Behandlung virusinaktiviertes Human plasma: Hersrellung und bisherige klinische Erfahrungen" *Infusionther Transfusionmed* 20(2): 19–24 (1993).

Mohr, et al. "Photo–Inactivaion of Viruses in Therepeutical Plasma" in *Virological Safety Aspects of Plasma Derivatives. Dev Biol Stand. Basel Karger.* (F. Brown, ed.) 81: 177–183 (1993).

Newman, et al. "Bad Blood" *US News and World Report* Jun. 27: 68–78 (1994).

Schneider, et al. "Methylene Blue and Rose Bengal Photoinactivation of RNA Bacteriophages: Comparitive Studies of 8–Oxoguanine Formation in Isolated RNA" *Arch. Biochem. Biophys.* 301(1):91–97 (1993).

Schneider, et al. "Methylene Blue plus light mediates 8–hydroxy 2'–deoxyguanosine formation in DNA preferentially over strand breakage" *Nuc. Ac. Res.* 18:631–635 (1990).

* cited by examiner

ANTIVIRAL THERAPY USING THIAZINE DYES

This is a divisional of U.S. Ser. No. 08/707,992, filed Jul. 12, 1996, now U.S. Pat. No. 5,827,644, which is a continuation U.S. Ser. No. 08/251,624, filed May 31, 1994, by Robert A. Floyd and Raymond F. Schinazi, entitled, "Antiviral Therapy Using Thiazine Dyes," now U.S. Pat. No. 5,571,666, issued Nov. 5, 1996, which is a continuation of U.S. Ser. No. 08/029,984, filed Mar. 12, 1993 by Robert A. Floyd and Raymond F. Schinazi for "Antiviral Therapy Using Thiazine Dyes," now abandoned, which is a continuation of U.S. Ser. No. 07/758,228 filed on Sep. 9, 1991 by Robert A. Floyd and Raymond F. Shinazi for "Antiviral Therapy Using Thiazine Dyes", now abandoned, which is a continuation of U.S. Ser. No. 07/632,606 filed on Dec. 24, 1990, now abandoned, which is a continuation of U.S. Ser. No. 07/350,383, entitled "Antiviral Therapy Using Thiazine Dyes" filed May 11, 1989 by Robert A. Floyd and Raymond F. Schinazi, now abandoned, which is a continuation-in-part of U.S. Ser. No. 07/264,088, filed Oct. 28, 1988, now U.S. Pat. No. 4,950,665, issued on Aug. 21, 1990.

This is a continuation-in-part of U.S. Ser. No. 264,088 entitled "Phototherapy Using Methylene Blue" filed Oct. 28, 1988 by Robert A. Floyd.

The United States government has rights in this invention by virtue of National Institutes of Health grant No. CA42854.

BACKGROUND OF THE INVENTION

This invention is generally in the area of methods for the treatment of viral diseases, and more specifically relates to the treatment of AIDS using thiazine dyes.

Methylene blue, 3,7-Bis(dimethylamino)phenothiazin-5-ium chloride, $C_{16}H_{18}ClN_3S$, is a dark green or blue thiazine dye which was first isolated in 1876. It is FDA approved for oral administration and has been reported to be effective as an antiseptic, disinfectant, and antidote for cyanide and nitrate poisoning. For over 50 years it has been known that methylene blue is reduced by mitochondria to leukodye which is then auto-oxidized back to methylene blue by oxygen, yielding $H_2O_2$. This is the probable mechanism by which methylene blue, injected i.v. at a dose of 1 mg/kg body weight, is effective in the treatment of methemoglobinemia, a clinical disorder where more than 1% of the hemoglobin in the blood has been oxidized to $FE^{3+}$. Kelner and Alexander reported in J. Biol. Chem. 260(28), 15168–15171 (1985), that methylene blue oxidizes glutathione directly when it is reduced by NADPH, rather than via the $H_2O_2$.

Methylene blue, in the presence of light, has been reported to damage DNA, probably by destroying or cleaving the DNA at the guanine residues. Simon and Van Vunakis, Arch. Biochem. Biophys. 105, 197–206 (1964), noted that the effect of several photoactive dyes and light is dependent on the concentration of the dye, as well as light wavelength and intensity, and can be correlated with uptake of oxygen and decrease in ultraviolet absorbance by guanine derivatives. Kornhauser, et al., Photochem. Photobiol. 18, 63–69 (1973) attempted to characterize the changes in guanosine following exposure to methylene blue and light using thin layer chromatographic analytical techniques.

Others have also attempted, without success, to analyze the actual mechanism of the effect of methylene blue and light on DNA. Friedman and Brown, Nucleic Acids Res. 5, 615–622 (1978), showed that methylene blue and light caused lesions at deoxyguanosines in DNA and that subsequent exposure to piperidine caused strand rupture. They hypothesized that cyclo-addition occurred at various positions in the purine ring, rendering the DNA susceptible to base catalyzed cleavage following modification of the other nucleoside bases.

Waskell, et al., reported in Biochim. Biophys. Acta 129, 49–53 (1966), that extensive irradiation of polynucleotides in the presence of methylene blue causes extensive destruction of guanosine, leaving ribose, guanidine, ribosylurea, and free urea. They postulated that the destruction of the guanosine residues was the mechanism for a previous observation by Sastry, et al., Biochim. Biophys. Acta, 129, 42 (1966), that, in vitro, methylene blue and irradiation inactivates Tobacco Mosaic Virus (TMV) RNA, rendering the virus uninfective. Singer and Fraenkel-Conrat, have also reported, in Biochem. 4, 2446–2450 (1966), that another type of dye, thiopyronin (where the ring N is replaced by CH), and proflavin, cause inactivation of TMV RNA in the presence of light. This is also the probable mechanism for the observation that topical administration of a 0.1% solution of methylene blue in conjunction with polychromatic light photoinactivates viruses such as herpes simplex, as referenced in American Hospital Formulary Service 92:00 Unclassified Therapeutic Agents, page 2176 editor, Gerald K. McEvoy (American Society of Hospital Pharmacists, Inc. 1981 revised 1988). Other observations have been made showing in vitro inactivation of viruses using light, methylene blue, and electricity, as reported in J. Clin.Microbiol., 17(2), 374–376 (1983), by Badylak, et al., (pseudorabies virus) and Proc.Soc.Exper.Biol.Med. 161, 204–209 (1979) by Swartz, et al., (Herpes simplex).

U.S. Ser. No. 264,088 entitled "Phototherapy Using Methylene Blue" filed Oct. 28, 1988 by Robert A. Floyd disclosed a method for using thiazine dyes, especially methylene blue, in combination with light to hydroxylate guanosine or deoxyguanosine at the C8 of the purine ring. The number of guanosines in a nucleic acid strand converted to 8—OH-deoxyguanosine (8—OH-dG) or 8—OH-guanosine (8—OH-G) can be controlled through manipulation of the concentration of methylene blue, light intensity and length of exposure, pH, and buffer strength. Very little, if any, other derivatives are formed. As described, the method can be used for the selective mutation or modification of either a DNA or a RNA sequence, or the protein expressed therefrom. 8—OH-dG and 8—OH-G do not base pair well and are especially susceptible to misreading.

Hydroxylation of guanine in DNA to produce 8-hydroxydeoxyguanosine (8—OH-dG) has been postulated to be an important factor in mutation and carcinogenesis by Kasai and Nishimura, Nucleic Acid Res. 12, 2137–2145 (1984); Gann. 75, 565–566 and 841–844 (1984); Environ. Health Perspect. 67, 111–116 (1986); Kasai, et al., Gann. 75, 1037–1039 (1984); Carcinogenesis 7, 1849–1851 (1986); Aida and Nishimura, Mutation Res. 192, 83–89 (1987). Kuchino, et al., Nature (London) 327, 77–79 (1987) used synthetic oligonucleotides containing 8-hydroxydeoxyguanosine in a specific position as a template for DNA synthesis to show misreading at the modified base and at adjacent pyrimidine bases. They observed that specific base-pairing was completely lacking at the 8-hydroxyguanosine and that incorrect bases were inserted at the adjacent pyrimidine bases. Kasai, et al., reported in Carcinogenesis 8(12), 1959–1961 (1987) that administration of a renal carcinogen, potassium bromate, to the rat caused a significant increase of 8-hydroxydeoxyguanosine in the kidney DNA, but not in non-target organ DNA.

Chemically, 8-hydroxydeoxyguanosine is made from guanosine by the action of reagents which generate oxygen radicals, such as ascorbic acid and other reducing agents, metals, polyphenols, and asbestos, and by x-irradiation. Intracellular DNA appears to undergo repair by enzymes following formation of 8-hydroxy-deoxyguanosine. This may be a naturally occurring response which has evolved to combat the effects of the many mutagens, tumor promoters, and carcinogens which cause the formation of 8-hydroxydeoxyguanosine.

As described in U.S. Ser. No. 264,088 issued as U.S. Pat. No. 4,950,665 on Aug. 21, 1990, the selective administration of thiazine dyes can be used in the treatment of viral infections and in cancer. Selective delivery can be achieved using systems such as liposomes for delivery to macrophages and other phagocytic cells or biodegradable controlled release implants. Viruses, bacteria, and cells undergoing rapid DNA synthesis are all inactivated by methylene blue when irradiated with light. Treatment can be extracorporeal or by light irradiation of specific tissues using other methods. Methylene blue absorbs in the red wavelengths, i.e., approximately 670 nm, which penetrates tissue much better than other lower wavlengths.

Acquired Immunodeficiency Syndrome (AIDS) is generally accepted at this time to be a consequence of infection with the retrovirus variously termed human T-lymphotropic virus type III (HTLV-III), lymphadenopathy-associated virus (LAV), AIDS associated retrovirus (ARV), or human immunodeficiency virus (HIV-1). There is considerable difficulty in diagnosing the risk of development of AIDS. AIDS is known to develop in at least 50% of the individuals infected with human immunodeficiency virus (HIV), although this percentage is suspected to be much higher.

A patient is generally diagnosed as having AIDS when a previously healthy adult with an intact immune system acquires impaired T-cell immunity. The impaired immunity usually appears over a period of eighteen months to three years. As a result of this impaired immunity, the patient becomes susceptible to opportunistic infections, various types of cancer such as Kaposi's sarcoma, and other disorders associated with reduced functioning of the immune system.

No treatment capable of preventing or curing HIV infection is currently available, although several compounds have demonstrated antiviral activity against the virus in vitro, including HPA-23, interferons, ribavirin, phosphonoformate, ansamycin, suramin, imuthiol, penicillamine, rifabutin, AL-721, 3'-azido-3'-deoxythymidine (AZT), and other 2',3'-dideoxynucleosides. AZT is the only drug which has been demonstrated to prolong life of patients infected with HIV. However, AZT is quite toxic when used for periods of several months and must be discontinued even in those patients initially tolerant to the drug due to the drug causing severe anemia. See Yarchoan et al., *Lancet*, 575–580 (1986). Further, AZT-resistant strains of HIV have now been reported in patients undergoing treatment with AZT, Larder, B. A., Darby G., Richmond, D. D., *Science* 243, 1731–1734 (1989).

Many inhibitors of cellular processes, such as AZT, limit viral replication, but are at the same time quite toxic for the host as well. Most of the antiviral drugs that have been discovered so far cannot be prescribed for a prolonged period of time because of their toxicity. Accordingly, it is clear that there is a strong need for new antiviral agents, especially those with low toxicity to normal cells. More particularly, because of the high mortality of AIDS and the lack of an effective treatment for this disease, there remains a great need for development of new low toxicity agents for prophylactic use as well as long term therapy of AIDS patients.

It is therefore an object of the present invention to provide methods and compositions for treatment or prevention of viral infections.

It is further object of the present invention to provide methods and compositions for selectively inactivating HIV.

SUMMARY OF THE INVENTION

A method for using thiazine dyes, especially methylene blue, alone or in combination with low levels of light, to selectively inactivate or inhibit intracellular replication of specific viruses, especially human immunodeficiency virus.

Examples of useful thiazine dyes are methylene blue, azure A, azure C, toluidine blue O, and thionine. The preferred dye at this time is methylene blue. Methylene blue is FDA approved for topical, i.v., and oral administration, and has minimal side effects. Selective delivery can be achieved using systems such as liposomes for delivery to macrophages and other phagocytic cells or using biodegradable controlled release implants. Since methylene blue absorbs in the red wavelengths, i.e., approximately 670 nm, which penetrates tissue much better than other lower wavelengths, light penetrating the skin to the capillaries at the surface can be used to enhance the activity of the dye.

BRIEF DESCRIPTION OF THE DRAWINGS

FIG. 1A is a bar graph; FIG. 1B is a line graph.

DETAILED DESCRIPTION OF THE INVENTION

Figure 1A:
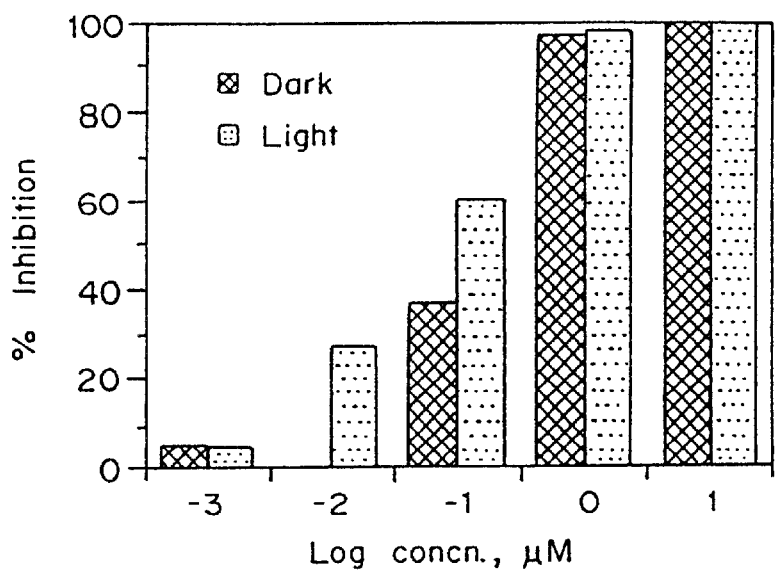
FIGS. 1A and 1B are graphs of the effect of methylene blue in the light and in the dark on the replication of HIV-1 in human PBM cells, % inhibition versus log concentration of methylene blue, $\mu$M.
Figure 1B:
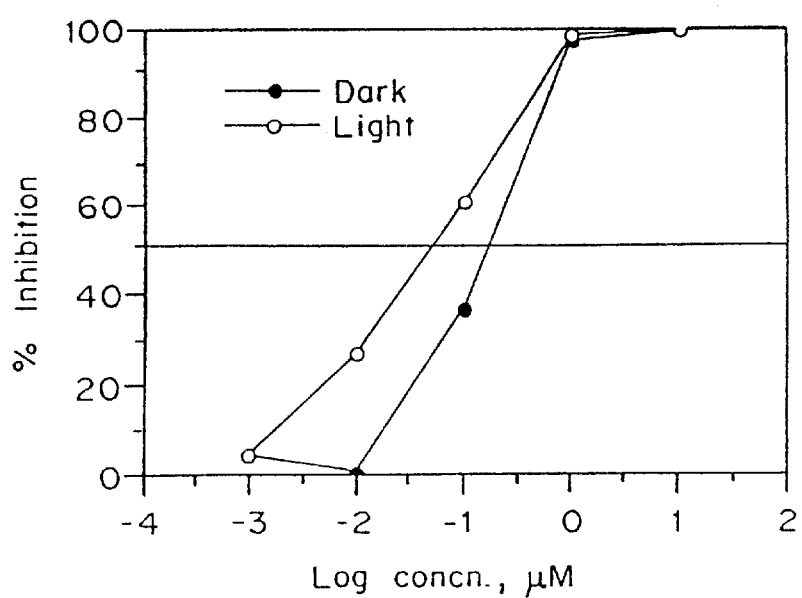

In co-pending application, U.S. Ser. No. 264,088 entitled "Phototherapy Using Methylene Blue" filed Oct. 28, 1988 by Robert A. Floyd, issued as U.S. Pat. No. 4,950,665 on Aug. 21, 1990, it was demonstrated that the thiazine dye methylene blue plus light hydroxylates both guanosine and deoxyguanosine to yield 8—OH-guanosine (8—OH-G) and 8—OH-deoxyguanosine (8—OH-dG), respectively. This treatment can be used to selectively, and in a controlled manner, to modify the guanine bases in viral DNA and RNA, both in vitro and intracellularly. 8—OH-G is used herein to refer to both 8—OH-G and 8—OH-dG unless otherwise stated.

The production of 8—OH-G results in mutations in nucleic acid since it does not base-pair as well as the unaltered guanosine and because the based adjacent to the 8—OH-G can be misread during replication, transcription, and translation. Viruses replicate within the host's cells, using enzymes encoded by their own genetic material and the host cell's "machinery". Replication usually occurs at a high rate, with much of the transcription and translation being involved in production of new virus. It has now been discovered that the dyes interfere with transcription and translation in the dark or in low light levels, as well as in light. Further, it has been discovered that some types of viruses are particularly sensitive to the thiazine dyes. Examples of these viruses are human immunodeficiency virus (HIV), and, to a lesser degree, Herpes simplex virus (HSV). Accordingly, the thiazine dyes can be used to treat infections by these viruses in vivo by interfering with the transcription and translation involved in replication of the virus in the host cells, at least in part by the mechanism whereby the dye hydroxylates the guanosine or deoxyguanosine to yield 8—OH-guanosine (8—OH-G) or 8—OH-deoxyguanosine (8—OH-dG), respectively. There is minimal effect on the host cell, presumably because of the lower rate of replication.

The activity of the dye can be enhanced further by irradiation with light or by derivatization with compounds such as antisense mRNA. The thiazine dye can also be provided in combination with other known antibiotics, anti-inflammatories, antifungals, and antivirals.

Thiazine dyes have been used in a variety of applications, as discussed in the Background of the Invention. However, the method described herein is based on the selective and controlled use of the compound, not the complete destruction of all genetic material, which would be completely inapplicable to any method wherein the goal is to preserve and minimize toxic effects to the host cells. Further, the method described herein does not require administration or exogenous light, although the results may be enhanced by exposure to light in addition to that normally transmitted through the skin.

Examples of useful thiazine dyes are methylene blue, azure A, azure B, toluidine blue O, and thionine. Methylene blue is the preferred dye at this time. These dyes are all commercially available from a number of different sources.

The dyes can be applied topically or systemically for in vivo applications. Both methods of administration are approved by the Federal Drug and Food Administration for methylene blue, although methylene blue is not FDA approved at this time for any topical or in vivo application for the treatment of viral infections. Methylene blue is a thiazine dye occurring as dark blue-green crystals which is soluble in water and sparingly soluble in alcohol, forming deep blue solutions. Methylene blue injectable has a pH of 3–4.5. The $pK_a$ is between 0 and −1.

*Drug Facts and Comparisons,* page 1655 (J. B. Lippincott Co., St. Louis, Mo. 1989) reports that methylene blue is useful as a mild genitourinary antiseptic for cystitis and urethritis, in the treatment of idiopathic and drug-induced methemoglobemia and as an antidote for cyanide poisoning. Recommended dosages are 55 to 130 mg three times daily, administered orally. Oral absorption is 53% to 97%, averaging 74%, DiSanto and Wagner, *J.Pharm.Sci.*61(7), 1086–1090 (1972). Pharmacopeia states that the recommended dose is 50 to 300 mg by mouth; 1 to 4 mg/kg body weight i.v. Side effects include blue urine, occasional nausea, anemia and fever, *American Hospital Formulary Service "Drug Information* 88" states that the recommended i.v. dosage for children is 1 to 2 mg/kg body weight, injected slowly over several minutes, which can be repeated after an hour. 55 mg tablets are available from Kenneth Manne. 65 mg tablets are available from Star Pharmaceuticals. Methylene Blue Injection (10 mg/ml) is available from American Reagent, Harvey, Kissimmee, Pasadena.

Narsapur and Naylor reported in *J.Affective Disorders* 5, 155–161 (1983) that administration of methylene blue orally, at a dosage of 100 mg b.i.d. or t.i.d., or intravenously, 100 mg infused over 10 min, may be effective in treating some types of mental disorders in humans, indicating that the dye may cross the blood-brain barrier and therefore have particular applicability in the treatment of viral infections of the brain and central nervous system. Methylene blue was administered for periods of one week to 19 months to adult humans, with minimal side effects.

The *American Hospital Formulary Service "Drug Information* 88" reports that methylene blue is absorbed well from the GI tract, with about 75% excreted in urine and via the bile, mostly as stabilized colorless leukomethylene blue. As reported by G. E. Burrows in *J.Vet.Pharmacol.Therap.,* 7, 225–231 (1984), the overall elimination rate constant of methylene blue, in sheep, is 0.0076±0.016 min$^{-1}$, with minimal methemoglobin production at doses as high as 50 mg/kg and no hematologic changes seen up to four weeks after a total dose of 30 mg/kg methylene blue. The 24 h $LD_{50}$ for intravenous methylene blue administered as a 3% solution was 42.3 mg/kg with 95% confidence interval limits of 37.3 to 47.9 mg/kg, demonstrating that methylene blue can be safely administered at a dosage of up to at least 15 mg/kg. As reported by Ziv and Heavner in *J.Vet. Pharmacol-.Therap.* 7,55–59 (1984), methylene blue crosses the blood-milk barrier easily.

The method described herein for the inhibition of HIV infections in vivo requires dosages in the range producing a blood concentration of approximately 20 to 200 micromolar, or 7.5 to 75 mg/l. The usual blood volume for babies is approximately 2.5 l, for adult humans it is approximately 10 l. Taking into account the 74% oral absorption and 75% excretion of that absorbed over a period of time, and assuming the lower therapeutic index in darkness than in light, this is approximately equivalent to 5.76 mg/kg over an 18 hour period.

The thiazine dyes can also be delivered using techniques known to those skilled in the art of drug delivery to target specific cell types or to enhance the activity of the dye. For example, a procedure utilizing injection of photoactive drugs for cancer treatment is described by Edelson, et al., in *New England J. Med.* 316, 297–303 (1987). Thiazine dyes can be specifically delivered to macrophages, a site of high HIV concentration in AIDS patients, using techniques such as liposome delivery. Liposomes are generally described by Gregoriadis, *Drug Carriers in Biology and Medicine* Ch. 14, 287–341 (Academic Press, NY, 1979). Methods for making light sensitive liposomes are described by Pidgeon, et al., in *Photochem.Photobiol.* 37, 491–494 (1983). Liposome compositions are commercially available from companies such as the Liposome Company, Inc., Princeton, N.J. Release of compounds from liposomes ingested by macrophages is described by Storm, et al., in *Biochim.Biophys.Acta* 965, 136–145 (1988).

Alternatively, the dye can be continuously delivered to a patient over an extended period of time using a controlled release polymeric implant. Polymeric implants are generally manufactured from polymers which degrade in vivo over a known period of time. Examples of useful polymers include polyanhydrides, polylactic acid, polyorthoester, and ethylene vinyl acetate. These devices are also commercially available. Alza Corporation, Palo Alta, Calif., and Nova Pharmaceuticals, Baltimore, Md., both manufacture and distribute biodegradable controlled release polymeric devices.

The present invention will be further understood with reference to the following non-limiting examples.

EXAMPLE 1

Selective Formation of 8-hydroxyguanine Using Methylene Blue and Light

Methylene blue plus light causes formation of 8-hydroxy-2'-deoxyguanosine (8—OHdG). The amount of 8—OHdG formed in DNA by methylene blue plus light increases as a function of time of exposure to white light and as the methylene blue concentration increases. The procedure used was as follows.

Methylene blue was added to calf thymus DNA solubilized in sodium phosphate buffer (0.0935 mg DNA/ml, 0.014 M Na Phosphate, pH 6.8) to produce a final concentration of 0.02 mM. The methylene blue containing DNA solution was then exposed to white light (100 watt incandescent light 11 cm from a beaker containing the sample being treated) in an ice bath. The treated DNA was precipitated with ethanol (400 $\mu$l 5 M NaCl in 5 ml ethanol), collected by centrifugation at 2000 rpm for one hr at 4° C., and the pellet redissolved in 250 $\mu$l Bis-Tris EDTA buffer containing 10 mM MgCl$_2$. The redissolved DNA was next placed in a boiling water bath for three min then cooled rapidly, digested with DNAse I (10 $\mu$g) and endonuclease (0.6 units) overnight at 37° C. The DNA was further digested to the free nucleotide level with phosphodiesterase (PDE) (Calbiochem snake venom, 0.04 units) and alkaline phosphatase from calf intestine (Calbiochem, 1 unit) overnight at pH 8.0 and 37° C. The pH of the solution was lowered to 4.0 with acetic acid and the volume was adjusted to 250 $\mu$l. The sample was filtered and run on HPLC to measure the concentration of 8-hydroxyguanosine. Methylene blue plus light clearly causes hydroxylation of guanine as shown in Table 1.

The nucleosides of adenine, cytosine, thymine, and guanine (approximately 200 nmoles each) were also subjected to methylene blue (20 $\mu$l into 2.0 mls final total volume) plus light treatment (100 watt incandescent light 11 cm over solution for 15 min). Only deoxyguanosine reacted to form the hydroxylated derivative, based on HPLC analysis.

Similar results are obtained when RNA is substituted for the DNA.

TABLE 1

Quantitation of 8-hydroxyguanosine in DNA exposed to methylene blue and light.

| Experimental Condition | Ratio of 8-OHdG to $10^5$ dG |
|---|---|
| DNA + Light | 6.8 |
| DNA + MB | 24.2 |
| DNA + Light + MB | 484.2 |

Data represent the average of 5 replicate samples

EXAMPLE 2

Inactivation of RNA Virus R17 Using Methylene Blue and Light

Exposure of the RNA virus R17 to 0.02 $\mu$M methylene blue plus light for 15 min (100 watt incandescent bulb at 11 cm) causes inactivation of R17, as assessed by its ability to form plaques on a bacterial lawn. The infectivity of the virus is inactivated 50% by a 45 seconds exposure to light in the presence of 0.05 $\mu$M methylene blue.

Add 20 $\mu$l $\phi$ (R17 phage) stock to 2.0 ml dilution buffer and dispense 0.3 ml into each of tubes A–F. Next add methylene blue to give concentrations shown in Table 2 below. Pipet 270 $\mu$l of samples to be light treated into the #1 wells of a 96 well microtiter plate, corresponding to its letter label A–H. The samples in the microtiter plate were exposed to light through water (¼ cm) deep in a petri dish for 5 minutes. 270 $\mu$l of each sample not to be light treated was then added to wells in the plate.

After treatment, viable R17 phage were titered by making serial 10× dilutions in the microtiter plate, adding 0.1 ml of selected dilution to 0.2 ml of log phase *E. coli* strain XL-1-Blue cells (approximately $10^7$ cells/ml), obtained from Stratagene, La Joya, Calif., and plating out 0.1 ml.

TABLE 2

Effect of methylene blue and light on the infectivity of RNA virus R17.

| MB conc. (uM) | Light 5' | pfu/ml |
|---|---|---|
| 0 | no | $7.20 \times 10^{11}$ |
| 0.02 | yes | $5.04 \times 10^{10}$ |
| 0.04 | yes | $1.11 \times 10^{10}$ |
| 0.2 | yes | $3.25 \times 10^5$ |
| 2.0 | no | $4.80 \times 10^{10}$ |
| 2.0 | yes | $3.00 \times 10^3$ |
| 20.0 | no | $3.00 \times 10^9$ |
| 20.0 | yes | $4.20 \times 10^4$ |

The methylene blue did not inhibit growth of the bacterial lawn at the concentrations used in the R17 inactivation and titering.

EXAMPLE 3

Effect of Duration of Light Exposure on the Inactivation of R17 Virus

R17 virus samples were also tested to determine the time of exposure of light required to inactivate the virus. The procedure was similar to that used for Example 2 as outlined above except that the concentration of MB was held constant at 0.05 uM while the time of exposure was varied. The length of exposure was varied as follows:

Add 0.3 ml to well H2, treat with light 0–5 min. Add 0.3 ml to well G2, treat with light 5 min–7.5 min. Add 0.3 ml to well F2, treat with light 7.5 min–9.0 min. Add 0.3 ml to well E2, treat with light 9.0 min–9.5 min. Add 0.3 ml to well D2, treat with light 9.5 min–9.9 min. Add 0.3 ml to well C2, treat with light 9.9 min–10.0 min. Add 0.3 ml to well B, no light. Add 0.3 ml to well A, no light. The results are shown in Table 3.

TABLE 3

Effect of time of exposure to light on infectivity of R17 virus treated with MB.

| Time (Min.) | PFU |
|---|---|
| none | $2.76 \times 10^9$/ml |
| 0.1' | $3.3 \times 10^9$/ml |
| 0.5' | $5.0 \times 10^9$/ml |
| 1.0' | $1.0 \times 10^9$/ml |
| 2.5' | $9.1 \times 10^7$/ml |
| 5.0' | $6.93 \times 10^7$/ml |
| 10.0' | $4.35 \times 10^6$/ml |

These results demonstrate that methylene blue and light inactivated R17 under these conditions at a rate of $t_{1/2}$= 0.8–1.0 minutes.

EXAMPLE 4

Anti-viral Effect of Methylene Blue on Human Immunodeficiency Virus (HIV), Compared with AZT Methylene blue was prepared as described above. AZT was synthesized and purified by a modification of the method of Lin and Prusoff (Lin, T. -S, and W. H. Prusoff, *J. Med. Chem.* 21, 109–112 (1978). Acyclovir (ACV) was obtained from the Burroughs-Wellcome Co.

HIV Antiviral Studies.

Cells: Human peripheral blood mononuclear cells (PBMC) from healthy HIV-1 seronegative and hepatitis B virus seronegative donors were isolated by Ficoll-Hypaque discontinuous gradient centrifugation at 1,000×g for 30 minutes, washed twice in phosphate-buffered saline (pH 7.2; PBS), and pelleted at 300×g for 10 minutes. Before infection, the cells were stimulated by phytohemagglutinin (PHA) at a concentration of 16.7 µg/ml, and 4 mM sodium bicarbonate buffer.

Retrovirus: HIV-1 (strain LAV-1) was obtained from Dr. P. Feorino (Centers for Disease Control, Atlanta, Ga.). The virus was propagated in human PBMC using RPMI 1640 medium, as described previously by McDougal, et al., ("Immunoassay for the detection and quantitation of infectious human retrovirus, lymphadenopathy-associated virus (LAV)," *J. Immun. Meth.* 76, 171–183, 1985) without PBA or fungizone and supplemented with 7% (v/v) interleukin-2 (Advanced Biotechnologies, Silver Spring, Md.), 7 µg/ml DEAE-dextran (Pharmacia, Uppsala, Sweden), and 370 U/ml anti-human leukocyte (alpha) interferon (ICN, Lisle, Ill.). Virus obtained from cell-free culture supernatant was titrated and stored in aliquots at −70° C. until use.

Inhibition of Virus Replication in Human PBMC: Uninfected PHA-stimulated human PBMC were uniformly distributed among 25 $cm^2$ flasks to give a 5 ml suspension containing about 2×10$^6$ cells/ml. Suitable dilutions of virus were added to infect the cultures. The mean reverse transcriptase (RT) activity of the inocula was 50,000 dpm/ml corresponding to about 100 $TCID_{50}$, as determined by Groopman, et al., (1987), "Characterization of Serum Neutralization Response to the Human Immunodeficiency Virus (HIV)," *AIDS Res. Human Retro.* 3, 71–85. The drugs, at twice their final concentrations in 5 ml of RPMI 1640 medium (supplemented as described above), were added to the cultures. Uninfected and untreated PBMC at equivalent cell densities were grown in parallel as controls. The cultures were maintained in a humidified 5% $CO_2$-95% air incubator at 37° C. for six days after infection at which point all cultures were sampled for supernatant RT activity. Previous studies had indicated that maximum RT levels were obtained at that time.

RT Activity Assay: A six milliliter aliquot of supernatant from each culture was clarified of cells at 300×g for 10 minutes. Virus particles were pelleted from 5 ml samples at 40,000 rpm for 30 minutes using a Beckman 70.1 Ti rotor and suspended in 200 µl of virus disrupting buffer (50 mM Tris-HCl, pH 7.8, 800 mM NaCl, 20% glycerol, 0.5 mM phenylmethyl sulfonyl fluoride, and 0.5% Triton X-100).

The RT assay was performed in 96-well microtiter plates, as described by Spira, et al. (1987), "Micromethod for Assaying the Reverse Transcriptase of LAV-HTLV-III/Lymphadenopathy-Associated Virus," *J. Clin. Microbiol.* 25, 97–99. The reaction mixture, which contained 50 mM Tris-HCl, pH 7.8, 9 mM $MgCl_2$, 5 mM dithiothreitol, 4.7 µg/ml $(rA)_n \cdot (dT)_{12-18}$, 140 µM dATP, and 0.22 µM [$^3$H]TTP (specific activity 78.0 Ci/mmol, equivalent to 17,300 cpm/pmol; NEN Research Products, Boston, Mass.), was added to each well. The sample (20 µl) was added to the reaction mixture which was then incubated at 37° C. for 2 hours. The reaction was terminated by the addition of 100 µl 10% trichloroacetic acid (TCA) containing 0.45 mM sodium pyrophosphate. The acid-insoluble nucleic acids which precipitated were collected on glass filters using a Skatron semi-automatic harvester. The filters were washed with 5% TCA and 70% ethanol, dried, and placed in scintillation vials. Four ml of scintillation fluid (Econofluor, NEN Research Products, Boston, Mass.) were added and the amount of radioactivity in each sample was determined using a Packard Tri-Carb liquid scintillation analyzer (model 2,000CA). The results were expressed in dpm/ml of original clarified supernatant. The procedures for the anti-HIV-1 assays in PBMC described above have been published recently (see Schinazi, et al., *Antimicrob. Agents Chemother.* 32, 1784–1789, December 1988).

HSV Preparation: Confluent HEp-2 cells, in a roller bottle (Falcon, 850 $cm^2$), were infected at an input multiplicity of 0.01 PFU per cell (to minimize production of defective viruses). During the two-hour absorption period, the cells were exposed to the virus inoculum diluted in absorption buffer (10 ml PBS containing 1% newborn calf serum and 0.1% glucose). The virus inoculum was then removed and replaced with Hanks' Minimum Essential Medium (MEM) containing 2% inactivated newborn calf serum, penicillin (100 U/ml) and streptomycin (100 µg/ml) (P and S), sodium bicarbonate (2 g/L) and HEPES (25 mM) (maintenance medium). The infected cells were incubated at 37° C. for 3 to 4 days, until the cells could be easily shaken from the plastic surface of the culture bottles. The cells were then collected by centrifugation, suspended in a small volume of spent culture fluid (5 ml per 2×10$^8$ cells) and sonicated 3 times for one min on ice. The disrupted cells were centrifuged (2,000 g for 15 min at 4° C. and the supernatant was diluted with an equal volume of sterile skimmed milk (as stabilizer) and aliquots were frozen at −70° C.

HSV Plaque Reduction Assay: Near confluent Vero (African Green Monkey) cells in 6-well plates were infected with 100 µl virus diluted in absorption buffer to give 100–200 plaques per well. The plates were then incubated at 37° C. for 1 hour with intermittent rocking every 15 minutes. The inoculum was aspirated and the compounds at different concentrations (dissolved in maintenance medium) were added to replicate wells. For these assays, 0.1% pooled human gamma globulin was included in the media. The plates were placed in 5% $CO_2$-95% air incubator and the plaques were allowed to develop for 48 h prior to fixation (buffered 10% Formalin acetate), staining (0.5% crystal violet in 20% $EtOH/H_2O$) and enumeration. The degree of inhibition (percent plaques of control) was calculated by counting the mean plaque counts for the different drug dilutions. The antiviral potency of the drugs was determined by estimating the $ED_{50}$, the drug concentration necessary to reduce the number of plaques by 50% relative to the virus control cultures. For routine antiviral drug screening, we used the F strain of HSV-1 and the G strain of HSV-2 (Ejercito, et al., "Characterization of Herpes Simplex virus Strains Differing in Their Effect on Social Behavior of Infected Cells," *J. Gen. Virol.* 2, 357–364 (1968)). For HSV plaquing, Vero cells (rather than a human cell line such as fibroblasts) were used since these cells do not induce interferon. Acyclovir (ACV) was used as a positive control for the studies on HSV.

Cytotoxicity Studies.

Toxicity in Vero (African Green Monkey) Cells: Vero cells in growth medium (2.5 ml) were added to 25 $cm^2$ flasks (Falcon) in duplicate at a concentration equivalent to one-tenth of cell confluency for each compound under test. After incubation at 37° C. in 5% $CO_2$-95% air for 24 hr, the test compound (2× final concentration), dissolved in 2.5 ml of the growth medium was added, and two flasks were harvested immediately by decanting the medium, washing once with 3 ml of PBS, and then incubating at 37° C. for 5 min with 3 ml of trypsin/EDTA (0.125%/0.02%). The cells dislodged from the flask were generally in clumps and were dispersed by repeated forceful pipetting of the suspension against the surface of the flask. To 1 ml of the well-dispersed cell suspension, 0.2 ml of trypan blue solution was added, and the number of cells were counted using a hemacytomer. Each day for the next 3 days, two of the remaining flasks were harvested in the manner just described for determination of cell number. Only data on day three are presented. This method has previously been described by Schinazi, et al., "Effect of Combination of Acyclovir, and Vidarabine or its 5'-monophosphate on Herpes Simplex Viruses in Cell Culture and in Mice," Antimicrob. Agents Chemother. 22, 499–507 (1982)).

PBM and CEM Cells Proliferation Assay: The drugs were evaluated for their potential toxic effects on uninfected PHA-stimulated human PBM cells and also in CEM cells. The cells were cultured with and without drug for 6 days at which time aliquots were counted for cell viability as described above.

Enzyme Assays: The preparation of the enzyme and the assay conditions used, were recently described by Schinazi, et al., Antimicrob. Agents Chemother. 33, 115–117 (1989). HIV-1 RT and cellular DNA polymerase alpha were isolated from infected and uninfected PHA-stimulated human PBM cells according to traditional methods (Eriksson, B., et al., Antimicrob. Agents Chemother. 31, 600–604, (1987); Furman, et al., Proc. Natl. Acad. Sci. USA 83, 8333–8337, (1986); Abrell, et al., J. Virol. 12, 431–439, (1973).

Assays. Reaction mixtures (100 µl) contained:

|  | RT | DNA pol. alpha |
|---|---|---|
| Tris-HCl, pH 8.0 | 100 mM | 100 mM |
| KCl | 50 mM | — |
| $MgCl_2$ | 2 mM | 6 mM |
| DTT | 5 mM | 5 mM |
| BSA | 400 µg/ml | 400 µg/ml |
| [$^3$H]dTTP, (Sp.act. 82.3 Ci/mmol) | 1 µM | 1 µM |
| dATP, dCTP, dGTP | — | 100 µM |
| Poly(rA)-oligo(dT)$_{12–18}$ | 3 µg/ml | — |
| Activated DNA | — | 200 µg/ml |

The reactions were started by the addition of 10 µl of purified enzyme, incubated at 37° C. for the indicated periods of time and processed as described in Eriksson, et al., Antimicrob. Agents Chemother. 31, 600–604 (1987).

Median-Effect Method: $EC_{50}$ and $IC_{50}$ values were obtained by analysis of the data using the median-effect equation (Chou, T., et al., "Quantitative Analysis of Dose-Effect Relationships: The Combined Effects of Multiple Drugs or Enzyme Inhibitors," Adv. Enz. Regul. 22, 27–55 (1984).

Results.

The effect of the thiazine dye methylene blue on cellular growth and proliferation was tested using PBM, Vero and CEM cell cultures. The cytotoxicity of MB, both in the presence and absence of light, was compared with that of AZT. The antiviral effect of MB was also examined using HIV-1, HSV-1 and HSV-2. The combined results of the cytotoxic and antiviral studies are shown in Table 4.

TABLE 4

Summary of antiviral and cytotoxicity studies on HIV and HSV Comparing Thiazine dyes: methylene blue, toluidine blue O, azure A, azure B, and thionin, AZT, and ACV.

| Treatment | Antiviral Effect: $EC_{50}$ (µM) | | | Cytotoxicity: $IC_{50}$ (µM) | | |
|---|---|---|---|---|---|---|
|  | HIV-1 | HSV-1 | HSV-2 | PBMC[a] | Vero[b] | CEM[c] |
| AZT | 0.00022 | >100 | >100 | 74.6 | 39.5 | 56.1 |
| MB light | 0.028 | ≧10 | ≧10 | 6.1 | 0.14 | 0.12 |
| MB dark | 0.14 | ≧10 | ≧10 | >1.0 | 0.66 | 2.22 |
| ACV light | >100 | 0.022 | 0.51 | >100 | 1,700 | >100 |
| ACV dark |  | 0.013 | 0.16 | — | — | — |

EXAMPLE 5

Measurement of P24 to Quantitate Inactivation of HIV by Methylene Blue

The efficacy of methylene blue as an antiviral agent was further demonstrated using an independent assay method. While the previous example measured RT activity, the present example utilizes a direct quantitation of a viral protein (P24) as an indicator of antiviral effectiveness.

Peripheral blood mononuclear (PBM) cells were infected with HIV and treated with methylene blue as described above. The $EC_{50}$ levels were calculated from enzyme immuno-assay (EIA) measurements of viral coat protein P24. The P24-specific EIA kit was purchased from Abbott Labs. As in Example 4, the effectiveness of methylene blue was compared with AZT, the results are shown in Table 5.

TABLE 5

Effect of MB against HIV (LAV-I) in human PBMC Determination of P24 Levels by EIA (Abbott Ag Kit)

| Treatment | Conc. µM | ng P24/ml | % Inhibition (corrected) | $EC_{50}$ µM |
|---|---|---|---|---|
| Uninfected control |  | −0.1 |  |  |
| Infected control |  | 336.0 |  |  |
|  |  | 370.5 |  |  |
|  |  | 370.5 |  |  |
|  | mean | 359.0 | 0.0 |  |
| AZT | 0.0001 | 360.7 | −0.5 |  |
|  | 0.001 | 266.2 | 25.8 |  |
|  | 0.01 | 36.1 | 89.9 | 0.0064 µM |
|  | 0.1 | 5.2 | 98.5 |  |
| M.B. Light | 0.001 | 370.5 | −3.2 |  |
|  | 0.01 | 370.5 | −3.2 |  |
|  | .1 | 302.2 | 15.8 |  |
|  | 1 | 5.1 | 98.6 | 0.024 |
|  | 10 | 2.2 | 99.4 |  |
| M.B. Dark | 0.001 | 356.0 | 0.8 |  |
|  | 0.01 | 270.2 | 24.7 |  |
|  | .1 | 287.2 | 20.0 |  |
|  | 1 | 84.1 | 76.6 | 0.33 |
|  | 10 | 5.4 | 98.5 |  |

EXAMPLE 6

The Effect of Methylene Blue on Isolated DNA Polymerase Alpha and HIV Reverse Transcriptase The effect of methylene blue on two DNA polymerizing enzymes, HIV reverse transcriptase (RT) and calf thymus DNA polymerase alpha (CT α pol), was also studied. The results clearly show that MB is effective at inhibiting reverse transcriptase mediated DNA polymerization. In order to inhibit DNA polymerase alpha directed DNA synthesis, ten fold more MB is required, as shown in Table 6.

TABLE 6

Effect of MB on HIV-1 reverse transcriptase (RT) and calf thymus DNA polymerase in the presence and absence of light.

| Enzyme | $IC_{50}$ ($\mu M$) | |
| --- | --- | --- |
|  | Light | Dark |
| HIV-1 RT | 9.2 | 10.0 |
| CT α pol. | 125 | 105.1 |

Modifications and variations of the method to selectively, and in a controlled manner, inhibit specific viruses such as HIV, and use thereof in the treatment of viral infections will be obvious to those skilled in the art from the foregoing detailed description. Such modifications and variations are intended to come within the scope of the appended claims.

We claim:

1. A method for the treatment of a patient afflicted with the human immunodeficiency virus, the method comprising:
    administering to the patient a thiazine dye in a concentration which is effective to induce the formation of 8-hydroxyguanosine in the human immunodeficiency virus to inactivate the virus.

2. The method of claim 1 further comprising exposing the patient to light of a wavelength for a period of time effective to enhance the activation of the dye and to enhance the formation of 8-hydroxyguanosine in the virus.

3. The method of claim 1 wherein the dye is methylene blue and is delivered in a dosage yielding a blood concentration of between approximately 20 and 200 micromolar.

4. The method of claim 1 wherein the dye is administered orally.

5. The method of claim 1 wherein the dye is administered intravenously.

6. The method of claim 1 wherein the dye is administered topically.

7. The method of claim 1 further comprising delivering the dye in combination with liposomes.

8. The method of claim 1 further comprising delivering the dye in a controlled release polymeric implant.

9. The method of claim 1 further comprising providing the thiazine dye in combination with a compound selected from the group consisting of antibiotics, anti-inflammatories, antifungals, and antivirals.

10. The method of claim 1 wherein the thiazine dye is administered in a pharmaceutically acceptable carrier.

* * * * *